(12) United States Patent
Guo

(10) Patent No.: US 8,202,693 B2
(45) Date of Patent: Jun. 19, 2012

(54) METHOD OF ISOLATION OF NUCLEIC ACIDS

(75) Inventor: Qi Guo, Suwanee, GA (US)

(73) Assignee: Omega Bio-Tek, Inc., Norcross, GA (US)

( * ) Notice: Subject to any disclaimer, the term of this patent is extended or adjusted under 35 U.S.C. 154(b) by 255 days.

(21) Appl. No.: 12/624,861

(22) Filed: Nov. 24, 2009

(65) Prior Publication Data

US 2011/0124851 A1    May 26, 2011

(51) Int. Cl.
*C12Q 1/68*      (2006.01)
*H01L 21/336*    (2006.01)
*H01L 21/8249*   (2006.01)

(52) U.S. Cl. ............... 435/6.12; 435/259; 435/235.1

(58) Field of Classification Search ............... 435/6.12, 435/259, 235.1
See application file for complete search history.

(56) References Cited

U.S. PATENT DOCUMENTS

| 4,668,618 | A | * | 5/1987 | Thornthwaite | 435/6.16 |
| 6,037,464 | A | * | 3/2000 | Kim | 536/25.42 |
| 6,617,105 | B1 | * | 9/2003 | Rudi et al. | 435/6.11 |

FOREIGN PATENT DOCUMENTS

CN    101532011    *   9/2009

OTHER PUBLICATIONS

English abstract of CN101532011.*

* cited by examiner

*Primary Examiner* — Kenneth R. Horlick
*Assistant Examiner* — Joyce Tung
(74) *Attorney, Agent, or Firm* — Sutherland Asbill & Brennan LLP

(57) ABSTRACT

A method of isolation of nucleic acids from a biological sample of cells comprising a combination of a solid phase cell nuclei isolation procedure with a solid phase nucleic acid isolation method.

20 Claims, 2 Drawing Sheets

M  293 Cells  Hela Cells

M  Fish Liver  Frog Liver

METHOD OF ISOLATION OF NUCLEIC ACIDS

FIELD OF INVENTION

The present invention relates to methods of isolation of nucleic acids from cells. More particularly, the present invention relates to the isolation of nucleic acids using magnetic polymeric beads that attract cell nuclei and nucleic acids released therefrom, and isolating the nucleic acids from cell nuclei-beads complexes.

BACKGROUND OF THE INVENTION

The isolation of DNA is an important step in many biochemical and diagnostic procedures. For example, the separation of nucleic acids from the complex mixtures in which they are often found is frequently necessary before other studies and procedures, e.g. detection, cloning, sequencing, amplification, hybridization, and so on, can be undertaken. The presence of large amounts of cellular or other contaminating material, e.g. proteins or carbohydrates, in such complex mixtures often impedes many of the reactions and techniques used in molecular biology. In addition, DNA may contaminate RNA preparations and vice-versa. Thus, improved methods for the isolation of DNA from complex mixtures, such as blood, cells, and tissues, are demanded, not only from the preparative point of view, but also in the many methods in use today which rely on the identification of DNA diagnosis of microbial infections, forensic science, tissue and blood typing, and detection of genetic variations.

Nucleic acid isolation methods generally require an initial nucleic acid isolation step, to separate the nucleic acid from materials, e.g. protein, which may interfere in the hybridization and amplification techniques which are used. A range of methods are known for the isolation of nucleic acids, but generally, these rely on a complex series of extraction and washing steps and are time consuming and laborious to perform. Classical methods for the isolation of DNA from complex starting materials, such as blood, blood products, tissues, or other biological materials, involve lysis of the biological material by a detergent or chaotrope, possibly in the presence of protein degrading enzymes, followed by extraction options such as solid phase extraction (such as silica spin columns) or phenol extraction followed with ethanol precipitation.

Recently, paramagnetic beads based technology has been used for DNA isolation due to the popularity of robotic liquid handling instruments. Most magnetic beads based methods rely on lysing the sample with a detergent or chaotrope followed by binding DNA with magnetic beads. Those procedures are normally time consuming and complicated. Isolated DNA obtained from those methods always has potential contamination issues from proteins, RNA and other substances from the sample. Contamination with those substances can interfere with the downstream applications leading to irreproducible or false results. For blood DNA isolation, hemoglobin and RNA contamination commonly result from current magnetic beads based methods. Also, the volume of blood sample is always a limiting factor for blood DNA isolation due to the limited handling volume of the instruments. The volume limitation of the starting blood sample volume has become a very important issue for isolating DNA from blood using automated processes.

Improvements in methods for isolating nucleic acids are, thus, continually being sought, and more recently, other methods have been proposed which rely upon the use of a solid phase. U.S. Pat. No. 5,234,809 for example, describes a method where nucleic acids are bound to a solid phase in the form of silica particles, in the presence of a chaotropic agent such as a guanidinium salt, and thereby separated from the remainder of the sample. WO 91/12079 describes a method whereby nucleic acids are trapped on the surface of a solid phase by precipitation, in which alcohols and salts are generally used as precipitants.

U.S. Pat. No. 6,617,105 described a method that uses solid phase particles to specifically or non-specifically bind cells from a sample, the collected cells are then lysed and DNA is bound to the same solid phase particles and separated. However, this method still has to use extra measures to remove contaminates such as RNA and proteins.

While such methods speed up the nucleic acid separation process, a need still exists for improved methods which are quick and simple to perform, which enable good yields to be obtained without significant losses, and in particular which are readily amenable to isolating nucleic acids from cells in mixtures or environments where they may be present at low concentrations, as a preparative first step in isolating nucleic acids from target cells in nucleic acid based cell detection procedures.

SUMMARY OF THE INVENTION

The present invention provides a novel approach to isolate nucleic acids which integrates cell nuclei isolation and nucleic acid purification by using, in certain embodiments, the same solid support for both cell nuclei attraction and nucleic acid purification. In one embodiment, the nucleic acid isolation method of the present invention is achieved by first lysing the cell membrane and binding the intact cell nuclei to a solid support. Then, the method involves lysing the nuclear membrane of the cell nuclei bound to the solid support, and releasing nucleic acids from the cell nuclei. The released nucleic acids further bind to the solid support using a precipitant, and can be later isolated from the solid support using conventional methods.

In one aspect, the present invention provides a method of isolating nucleic acids from a biological sample of cells, said method comprising: a) contacting a sample containing cells with a cell membrane lysis solution in the presence of a solid support, to selectively lyse cell membranes over nuclear membranes, and wherein intact cell nuclei non-specifically bind to said solid support; b) separating intact cell nuclei bound to said solid support from cell membrane lysis supernatant; c) contacting the intact cell nuclei bound to said solid support with a nuclear membrane lysis solution to lyse nuclear membranes; and d) contacting the solution containing lysed nuclear membranes and solid support with a precipitant to non-specifically bind nucleic acids to said solid support. In certain embodiments, the inventive method of isolating nucleic acids from a biological sample of cells further comprises a later step of isolating nucleic acids from said solid support.

In yet other embodiments, the present invention provides a method of isolating nucleic acids from a biological sample of cells, said method consisting essentially of one or more of the above steps or others described herein.

The solid support as used in the present invention comprises spherical particles, including, but not limited to monodisperse particles having uniform size and reproducibility of reaction. In certain embodiments, the solid support comprises non-magnetic, magnetic, or superparamagnetic polymeric beads that may or may not be coated with different types of functionalized surfaces, such as positive or negative charges, hydrophilic or hydrophobic surfaces. In other embodiments, the magnetic polymeric beads may also be coated with a binding enhancing agent, including, but not limited to, DNA binding proteins, complementary DNA or RNA sequences, zippers, histones, and intercalating dyes.

The present invention thus provides, in certain embodiments, a method of isolating nucleic acids from a biological sample of cells comprising lysing the cell membrane with a cell membrane lysis buffer in the presence of magnetic polymeric beads, wherein the intact cell nuclei are released and non-specifically bind to the magnetic polymeric bead to form cell nuclei-bead complexes, which are then precipitated and separated from the cell membrane supernatant by applying a magnetic field. The precipitated and separated cell nuclei-bead complexes are then treated with a nuclear membrane lysis buffer so that the nuclear membrane is lysed and the nucleic acids are released from the lysed cell nuclei and bind non-specifically to the magnetic polymeric beads using a precipitant, such as alcohol, salt, detergent, polyethylene glycol, or a combination thereof.

In certain embodiments, the present invention provides that the cell membrane lysis solution comprises a nonionic surfactant, such as nonyl phenoxylpolyethoxylethanol (NP-40), polyethylene glycol p-(1,1,3,3-tetramethylbutyl)-phenyl ether (TRITON X-100), octy glycoside, within a range of about 0.1 to 5% v/v in the lysis solution/buffer. The cell membrane lysis solution can also be a buffer. In certain embodiments, the cell membrane lysis solution has pH of about 5-8, 7.5-8.0, or 6.5-7.5. In one embodiment, the cell membrane lysis solution comprises 10 mM Tris base (2-Amino-2-(hydroxymethyl)-1,3-propanediol, or TRIZMA® base), pH 7.5-8.0, 0.5% NP-40, 40 mM sodium citrate, and 3 mM $MgCl_2$. In another embodiment, the cell membrane lysis solution comprises 10 mM Tris base, pH 7.5-8.0, 0.5-1.0% TRITON X-100, 40 mM sodium citrate, and 3 mM $MgCl_2$. Selective, lysis of cell membranes over nuclear membranes may be achieved in any known or convenient manner. In one aspect of the present invention, the cell membrane lysis solution lyses the cell membrane preferentially over the cell nuclear membrane, so that the intact cell nuclei are released and are able to bind non-specifically to the solid support, e.g. magnetic polymeric beads, in the mixture.

The present invention further provides that the cell nuclei bound to the solid support in the mixture are separated from the cell membrane mixture, e.g. by magnetic force, and subjected to a treatment with a nuclear membrane lysis solution. The nuclear membrane lysis solution can comprise a detergent, a chaotrope, or a combination thereof. The nuclear membrane lysis solution can also be a buffer. Suitable detergents used in the nuclear membrane lysis solution include, but are not limited to sodium dodecyl sulfate (SDS), lithium dodecyl sulfate, and sodium lauroyl sarcosinate (sarkodyl). Suitable chaotropes used in the nucleic membrane lysis solution include, but are not limited to guanidium hydrochloride (GHCl), guanidium thiocyanate (GTC), sodium iodide (NaI), perchlorate, and lysis enzymes. In one embodiment, the nucleic membrane lysis solution comprises 1% (w/w) sarkosyl and 4 M GTC.

Lysis of cell nuclear membrane may be achieved in any known or convenient manner. One aspect of the present invention requires concentrating the cell nuclei by their non-specific binding to a solid support, e.g. magnetic polymeric beads, and separating the cell nucleus-bead complexes from the cell membrane supernatant, so that the nucleic acids released from the cell nuclei will be isolated or purified in a more concentrated or enriched environment than the environment mixed with various cellular components, thus, improving the nucleic acid isolation process.

The present invention offers a significant advantage over other existing DNA isolation methods when process large volume biological samples such as blood on robotic platform. For example, one of major bottleneck factors for the automated processing of high throughput blood DNA isolation is the sample volume which is limited by fixed volume of laboratory ware on the robot instrument. Current blood DNA isolation methods require around 3-4 times of sample volume in the initial step to create lysis and binding condition for the solid support, therefore the maximum volume of the biological samples can be handled are significantly limited due to the limited capacity of the vials or plates that can be handled in a instruments. By using the present invention, the volume or reagents added in the initial process step can be significantly reduced, for example by adding only up to 20% of original sample volume. For example, most conventional method can only handle around 300 µl blood sample on 96-well plate format due to the limited capacity of the plate. For 300 µl blood, it normally requires about 600 µl additional reagents to create lysis and binding condition for the solid support. By using the present invention, 60 µl lysis buffer can be used in the initial lysis step. Thus, much larger sample volume can be processed by using the present invention. For example, most conventional methods can only process up to 250 µl blood sample in a 1 ml 96 deep well plate, while the present invention method can process up to 800 µl blood sample. By removing cytoplasm and other supplement components in the initial lysis step, the present invention method removes all major contaminants such as hemoglobin, RNA and proteins through the initial lysis and separation steps. Therefore, RNase treatment is not necessary and proteinase treatment is significantly reduced or eliminated. Thus, the present invention advantageously enables automation, particularly when magnetic particles are used as the support, and reduces the time to obtain a very reliable and high yield of nucleic acids. The present invention further provides that the nucleic acids can be further released from the lysed cell nuclei and bind non-specifically to the solid support, e.g. the magnetic polymeric beads, using a precipitant, such as alcohol, salt, detergent, polyethylene glycol, or a combination thereof.

Thus, the present invention provides a quick, simple, and high throughput method of isolating nucleic acids for use in later nucleic acid based biochemical and diagnostic detection procedures.

DETAILED DESCRIPTION OF THE DRAWINGS

DETAILED DESCRIPTION OF THE INVENTION

Figure 1:
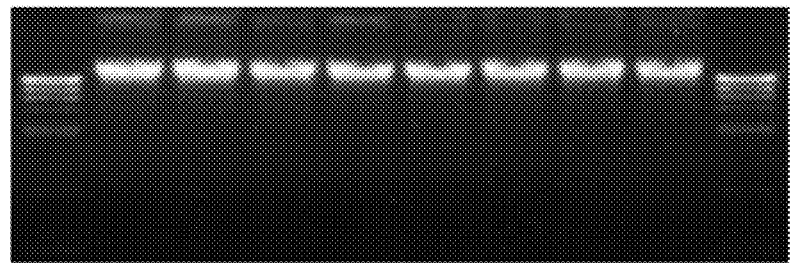
FIG. 1 shows the results on EtBr-stained agarose gel electrophoresis of the separation of genomic DNA obtained from 200 µl human whole blood.

In one embodiment, the present invention provides a novel method of isolation of nucleic acids from a biological sample of cells, in which cell membranes are first lysed with a cell membrane lysis solution while keeping the cell nuclei intact. The cell nuclei are released from the lysed cell and bound to a solid support, e.g. magnetic polymeric beads, to form cell nucleus-bead complexes, which are then separated from cell membrane supernatant. The cell nucleic membrane is then lysed with a nuclear membrane lysis solution so that nucleic acids inside the cell nucleus are released and later bound to the same solid support, e.g. magnetic polymeric beads, using a precipitant. The bound nucleic acids are further eluted and/ or isolated from the solid support in any known or convenient manner.

In one aspect, the present invention provides the combination of a cell nucleus purification procedure with a solid phase binding in which the intact cell nuclei are first isolated and bound to a solid support after the cell membrane is lysed, with subsequent solid phase isolation of the nucleic acid after the nuclear membrane is lysed.

As used herein, nucleic acids refer to DNA, rRNA or any naturally occurring or synthetic modification thereof, and combinations thereof. In certain embodiments, the nucleic acids are DNA, which can be single, double or triple stranded or in any other form, linear or circular.

As used herein, the sample of cells refers to any material containing nucleic acid within a nuclear membrane within such cells. For example, the samples can be obtained from materials from foods and allied products, clinical and environmental samples. In certain embodiments, the sample of cells is a biological sample, which contains eukaryotic cellular material. In certain embodiments, such biological material comprises all types of mammalian and non-mammalian animal cells, plant cells and bacteria. Representative samples include whole blood and blood-derived products, such as plasma or buffy coat, saliva, semen, tissue homogenates, urine, faeces, cerebrospinal fluid or any other body fluids, tissues, cell cultures, cell suspensions etc. Biological material also includes environmental samples such as soil, water, or food samples. The sample may also include relatively pure or partially purified starting materials, such as semi-pure preparations obtained by other cell separation processes.

As used herein, the form "nucleus isolation media" is interchangeably used with a "cellular membrane lysis solution." The nucleus isolation media or cellular membrane lysis solution used herein refers to a solution or buffer that selectively lyses cell membranes, while minimally or insignificantly lysing nuclear membranes, so that the cell nuclei are generally kept intact and can be isolated from the cell membrane supernatant.

In order to isolate cell nuclei, it is preferable to establish a medium that mirrors the external fluid of the tissue from which the cell nuclei are to be examined, i.e., the area about the cell in question, and to this end animal-to-animal and tissue-to-tissue variations exist. Thus, while the present invention is described essentially with reference to studies of human-derived tissue, it is understood that through suitable adjustments one may deal with other animal tissues as well. A medium hospitable to cell nuclei should have an ionic content comparable to the tonicity of the fluid external to the cell, i.e., a tonicity substantially similar or identical the area about the cell in question. Isotonicity is a relevant consideration for the nucleus isolation media of the present invention.

Another aspect of the nucleus isolation media is to include a minor amount of a nonionic surfactant. Suitable nonionic surfactants are described in McCutcheon's Detergents and Emulsifiers (Glen Rock, N.J.: McCutcheon Division, MC Pub. Co., 1981), including, but not limited to NP-40, an octylphenol ethylene oxide condensate with an average of 9 moles of ethylene oxide available as a 27% solution from Accurate Scientific and Chemical Co.; TRITON X-100, an octylphenoxy polyethoxy ethanol available from Rohm & Haas, and octy glycoside, a 1-0-n-octyl-beta-d-glycopyranoside available from Sigma Chemical Co. The present invention contemplates or combination any suitable surfactant that is determined by empirical selection and evaluation, which is capable of lysing the cell membrane selectively over the nuclear membrane.

In one embodiment, surfactant NP-40 or TRITON X-100 is included in the media in the range of about 0.1 to about 5% v/v, preferably, in the range of about 0.6 to about 2% v/v. In yet other embodiments, the nucleus isolation media has a pH of about 5 to about 8, preferably from about pH 6.5 to about pH 7.5. The specific pH can be preferably selected to be equivalent to the physiological pH of the animal in question. A buffer or buffer system is also included as an optional ingredient to maintain the pH of the media. In one embodiment, the cellular membrane lysis solution or nucleus isolation media comprises: 10 mM Tris pH 7.5-8.0, 0.5% NP-40, 40 mM Sodium Citrate, and 3 mM $MgCl_2$. In another embodiment, the cell membrane lysis solution or nuclei isolation media comprises: 10 mM Tris pH 7.5-8.0, 0.5-1% TRITON X-100, 40 mM Sodium Citrate, and 3 mM $MgCl_2$.

Binding of the cell nuclei to a solid support is achieved in any known or convenient manner. For example, non-specific binding of the cell nuclei to the support is achieved by appropriate choice of the solid support and conditions, e.g. the chemical or physical nature of the surface of the solid support, (e.g. hydrophobicity or charge), the pH or composition of the isolation medium. Appropriate buffers are used as media to achieve conditions appropriate for cell nuclei binding by simply bringing the solid support and the sample into contact in an appropriate medium. Conveniently, a buffer of appropriate charge and osmolarity is added to the sample prior to, simultaneously with, or after contact with the solid support.

The various components are mixed and simply allowed to stand for a suitable interval of time to allow the cell nuclei to bind to the solid support. The solid support can then be removed from the solution by any convenient means, which depends on the nature of the solid support, and includes all forms of withdrawing the solid support away from the sample supernatant, or vice-versa, including, but not limited to centrifugation, decanting, or pipetting.

The conditions for cell nuclei binding to a solid support are convenient, for example, by simply mixing the sample with a cell membrane lysis solution or cell nucleus isolation media in the presence of a solid phase or before or after combining with a solid phase, and allowing it to stand at room temperature, for 5 to 30 minutes or more, preferably, 20 minutes, before separating. Longer periods, e.g. 20 minutes to 3 hours, or even overnight, can also be used, if convenient. Mixing is done by any convenient means, including for example simple agitation by stirring or vortexing. Also, if desired, higher or lower temperatures may be used, but are not necessary.

The solid support may be any of the well-known supports or matrices which are currently widely used or proposed for immobilization or separation. These may take the form of particles, sheets, gels, filters, membranes, fibres, capillaries, or microtitre strips, tubes, plates or wells. Conveniently the support may be made of glass, silica, latex or a polymeric material. Preferred are materials presenting a high surface area for binding of the cells, and subsequently, of the nucleic acid. Such supports will generally have an irregular surface and may be for example porous or particulate, e.g. particles, fibres, webs, sinters or sieves. Particulate materials, e.g.

beads, are generally preferred due to their greater binding capacity, particularly polymeric beads.

Conveniently, a particulate solid support used according to the present invention comprises spherical beads. The size of the beads is, for example, on the order of diameter of at least 0.2 µm and preferably at least 1 µm, and has a maximum diameter of preferably not more than 10 and more preferably not more than 6 µm. For example, beads of diameter 0.2 µm to 1 µm work well.

The beads are preferably added either before, or together with, the cell membrane lysis solution or buffer. Alternatively, beads can be added after the cell membrane lysis step. In certain embodiments, the magnetic beads with cell nuclei attached thereon are separated from cell membrane supernatant by application of a magnetic field, e.g. using a permanent magnet. It is usually sufficient to apply a magnet to the side of the vessel containing the sample mixture to aggregate the particles to the wall of the vessel and to pour away the remainder of the sample. In certain embodiments, superparamagnetic particles or beads are used since magnetic aggregation and clumping of the particles/beads during reaction can be avoided, thus ensuring uniform and nucleic acid isolation. In certain embodiments, the SERA-MAG® Magnetic Particles or SERA-MAG® Magnetic Particles from Thermo Scientific (Indianapolis, Ind.) are used in the present invention.

Following cell nuclei binding, the isolated or support-bound cell nuclei are lysed to release their nucleic acid. Methods of lysing cell nuclei using a nucleus lysis solution are well known in the art and widely described in the literature, and any of the known methods can be used. For example, the following may be used: detergent lysis using, e.g. SDS, LiDS or sarkosyl in appropriate buffers; the use of chaotropes such as guanidium hydrochloride (GHCl), guanidium thiocyanate (GTC), sodium iodide (NaI), perchlorate, etc.; or enzymatic lysis. Again, all such methods are standard lysis techniques and are well known in the art, and any such method or combination of methods can be used.

Conveniently, nucleic membrane lysis can be achieved by using a lysis buffer comprising chaotropes and/or detergents. For example, the combination of a chaotrope with a detergent is found to be particularly effective. An exemplary suitable nuclear membrane lysis solution includes a chaotrope, such as GTC or GHCl, and a detergent, such as SDS or Sarkosyl. The nucleic membrane lysis agents are supplied in a simple aqueous solution, or included in a buffer solution, to form a so-called "lysis buffer". Any suitable buffer can be used, including for example TRIS, BICINE, TRICINE and phosphate buffers. Alternatively, the nuclear membrane lysis agents are added separately. Suitable concentrations and amounts of lysis agents vary according to the precise system and can be appropriately determined. In one embodiment, the nuclear membrane lysis solution comprises 2M to 7M chaotropes, such as GTC GHCl, NaI or perchlorate, and 0.1 to 50% (w/v) or 0.5 to 15% (w/w) detergent. In another embodiment, a suitable representative nuclear membrane lysis solution comprises an aqueous solution of 4M GTC, and 1% (w/v) sarkosyl.

To carry out the method of the present invention, the isolated, support-bound cell nuclei, are conveniently separated and isolated from the remainder of the sample, thereby concentrating or enriching the cell nuclei. Thus, the cell nuclei binding step serves to enrich the cells or to concentrate them in a smaller volume than the initial sample. Nucleic membrane lysis is conveniently achieved by adding an appropriate nucleic membrane lysis buffer containing the desired lysis agents or by subjecting the isolated cell nuclei to the desired lysis conditions. For example, in the case of simply adding a lysis buffer containing appropriate lysis agents, the isolated cell nuclei are simply incubated in the presence of the lysis buffer for a suitable interval to allow lysis to take place. Different incubation conditions may be appropriate for different lysis systems, and are known in the art. For example, for a detergent and/or chaotrope containing lysis buffer, incubation may take place at room temperature or at higher temperatures, e.g. 37° C. or 65° C. Likewise, time of incubation may be varied from a few minutes, e.g. 10 minutes to 30 minutes. In the case of GTC/Sarkosyl lysis buffers, incubation at, e.g. 25° C. for 3-5 minutes is found to be appropriate, but this may be varied according to need. For enzymatic lysis, e.g. using proteinase K, a longer treatment time is desired.

Following nucleic membrane lysis, the released nucleic acid is bound to the same support to which the lysed cell nuclei are bound in preferred embodiments. This nucleic acid binding is achieved in any way known in the art for binding nucleic acid to a solid support. Conveniently, the nucleic acid is bound non-specifically to the support, i.e., independently of sequence. Thus, for example the released nucleic acid can be precipitated onto the support using any of the known precipitants for nucleic acid, e.g. alcohols, alcohol/salt combinations, and polyethylene glycols (PEGs). Precipitation of nucleic acids onto a solid support, e.g. beads in this manner, is described for example in WO 91/12079. Salt may be added to the support and released nucleic acid in solution, followed by addition of alcohol which causes the nucleic acid to precipitate. Alternatively, salt and alcohol can be added together, or the salt can be omitted. Any suitable alcohol or salt can be used, and appropriate amounts or concentrations may readily be determined.

Alternative non-specific nucleic acid-support binding techniques include the use of detergents are described, e.g. in WO 96/18731 of Dynal AS (the so-called "DNA Direct" procedure), and the use of chaotropes for a nucleic acid-binding solid phase such as silica particles, is also described, e.g. in EP-A-0389063 (Akzo N.V.). Ionic binding of the nucleic acid to the support may be achieved by using a solid support having a charged surface, for example a support coated with polyamines.

The support which is used in the method of the present invention can also carry functional groups which assist in the specific or non-specific binding of nucleic acids, for example, DNA binding proteins, e.g. leucine zippers or histones or intercalating dyes (e.g. ethidium bromide or Hoechst 42945) which can be coated onto the support. Likewise, the support can also be provided with binding partners to assist in the selective capture of nucleic acids. For example, complementary DNA or RNA sequences, or DNA binding proteins can be used. The attachment of such proteins to the solid support is achieved using techniques well known in the art.

A convenient method of precipitating the nucleic acid according to the present invention is by adding a precipitant, e.g. alcohol, to the mixture containing the support and lysed cell nuclei. An appropriate volume of alcohol, e.g. 100% or 96% ethanol, is simply added to the mixture, and incubated for a time period sufficient to allow the released nucleic acid to bind to the support. The incubation conditions for this step can simply comprise incubating at 5-10 minutes at room temperature. However, the length of time can be varied, and temperature increased according to choice.

Optionally, it can be convenient to introduce one or more washing steps to the isolation method of the present invention, for example, following the nucleic acid binding step. Any conventional washing buffers or other media can be used. Generally speaking, low to moderate ionic strength buffers are preferred, e.g. 20 mM Tris-HCl at pH 8.0/20 mM C$_2$H$_3$NaO$_2$. Other standard washing media, e.g. containing alcohols, can also be used, if desired, for example washing with 70% ethanol.

The use of magnetic particles/beads of the present invention permits easy washing steps simply by aggregating the particles/beads, removing the nucleic acid binding medium, adding the washing medium, and reaggregating the particles/beads as many times as required.

Following the nucleic acid isolation process and any optional washing steps as desired, the support carrying the bound nucleic acid is transferred, e.g. resuspended or immersed into any suitable medium, e.g. water or low ionic strength buffer. Depending on the support and the nature of any subsequent processing desired, it may or may not be desirable to release the nucleic acid from the support. In the case of a particulate solid support, such as magnetic or non-magnetic beads, nucleic acids bound to the beads can in many cases be used directly, for example in PCR or other amplifications, without eluting the nucleic acid from the beads. Also, for many DNA detection or identification methods elution is not necessary since, although the DNA may be randomly in contact with the bead surface and bound at a number of points by hydrogen bonding or ionic or other forces, there are generally sufficient lengths of DNA available for hybridization to oligonucleotides and for amplification.

However, if desired, elution of the nucleic acid can readily be achieved using known means, for example by heating, e.g. to 65° C. for 5 to 10 minutes, following which the support/beads to be removed from the medium, and leaving the nucleic acids in solution. Such heating is automatically obtained in PCR by the DNA denaturation step preceding the cycling program.

The present invention provides a quick and simple nucleic acid isolation method with an appropriate combination of cell membrane lyisis, cell nuclei-binding, cell nucleic membrane lysis, and nucleic acid binding steps. The present invention thus provides a method which reliably and simply yields isolated nucleic acid in a short period of time, in many cases, less than one hour, or even less than 40 minutes. The simplicity of the present method allows for high throughput of samples. Concomitantly, the cell nucleic binding step, results in an enrichment or concentration of the cell nuclei and nucleic acids, thereby improving the nucleic acid isolation process. The present invention is also advantageously amenable to automation, particularly if particles, and especially magnetic particles, are used as the support.

Furthermore, the present invention has particular utility as a preliminary first step to prepare nucleic acids for use in nucleic acid-based detection procedures. Thus, a further aspect of the present invention is the use of the nucleic acid isolation method as hereinbefore defined in the preparation of nucleic acids for use in a nucleic acid-based detection method. Advantageously, the bound nucleic acids need not be eluted or removed from the support prior to carrying out the detection step, although this may be performed if desired. Whether or not the nucleic acid is eluted may also depend on the particular method which was used in the nucleic acid binding step. Thus, certain nucleic acid-binding procedures allow binding the nucleic acid to the support more tightly than others. In the case of DNA-binding using detergents (e.g. by DYNAL® DNA DIRECT, Invitrogen, Calif.) for example, the nucleic acids are eluted from the solid support when an elution buffer or other appropriate medium is introduced. Nucleic acids bound by means of a precipitant such as alcohol or a chaotrope, remain more tightly bound, and may not be eluted when placed in a buffer medium, and may require heating to be eluted.

Thus, the support-bound nucleic acids obtained from the present invention can be used directly in a nucleic acid based detection procedure, especially if the support is particulate, simply by resuspending the support in, or adding to the support, a medium appropriate for the detection step. Alternatively, the nucleic acids can be eluted into the medium if desired, but not necessarily required.

The present invention also provides kits for isolating nucleic acids comprising or consisting essentially of any of the above cell membrane lysis solutions, solid supports and nuclear membrane lysis solutions.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Other features and advantages of the invention will be apparent from the following description of the preferred embodiments thereof and from the claims. These and many other variations and embodiments of the invention will be apparent to one of skill in the art upon a review of the appended description and examples.

EXAMPLES

Example 1

Isolation of Genomic DNA from 200 µl Human Whole Blood

DNA Isolation: 0.2 ml whole human blood was mixed with 500 µl of cell membrane lysis buffer (1% TRITON X-100, 40 mM sodium citrate, 3 mM MgCl2) and 10 µl beads (50 mg/ml) in a microcentrifuge tube. The mixture was inverted 10 times and incubated at room temperature for 3 minutes, then the tube was placed in a magnet stand (Omega Bio-Tek, Atlanta, Ga.) for 7 minutes. The cell membrane supernatant was carefully removed. 300 µl of nuclear membrane lysis buffer (3.5 M Guanidine Hydrochloride, 20 mM Tris-HCl pH 7.4,) and 10 ul proteinase K (20 mg/ml) was added and incubated at 65° C. for 10 minutes. Then 200 µl of 100% isopropanol was added and the incubation continued for 5 minutes at room temperature. The beads were attracted to the tube wall with the magnet and the supernatant removed. The complex was washed twice with 500 µl 70% EtOH. All of the ethanol was removed and 50 µl water added. To remove residual ethanol the tubes were incubated at 65° C. for 10 minutes with an open lid. The isolated genomic DNA obtained through the present invention is shown in FIG. 1 on EtBr-stained agarose gel electrophoresis.

Figure 2:
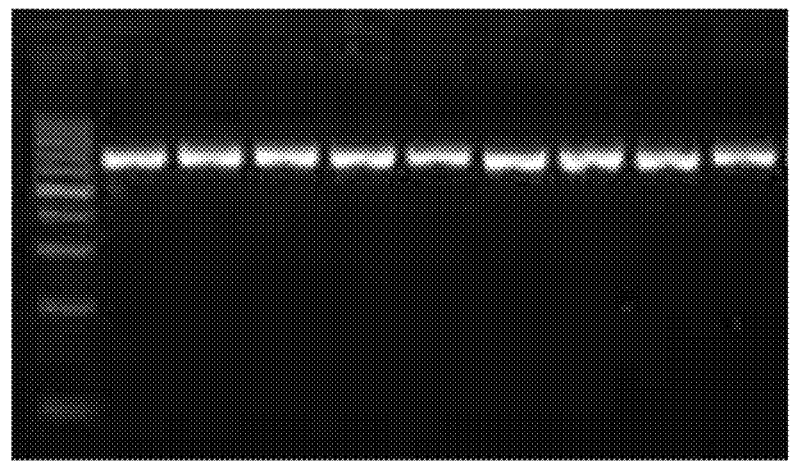
FIG. 2 shows the results on EtBr-stained agarose gel electrophoresis of the separation of PCR amplification products of DNA obtained from 200 µl human whole blood.

PCR amplification: The region for gene coding for human beta-actin was amplified. Amplifications were done using the standard protocols. (See FIG. 2).

Example 2

Isolation of Genomic DNA from 3 ml Human Whole Blood

Figure 3:
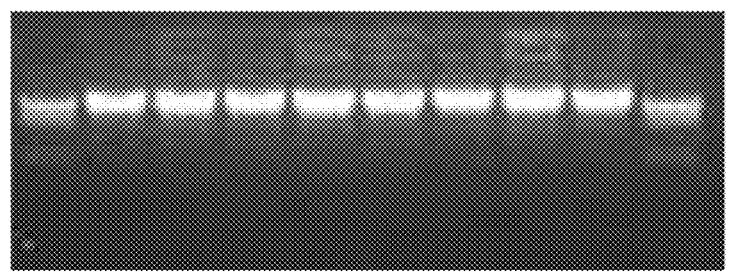
FIG. 3 shows the results on EtBr-stained agarose gel electrophoresis of the separation of genomic DNA obtained from 3 ml human whole blood.

DNA isolation: 3 ml whole human blood was mixed with 2 ml of cell membrane lysis buffer (0.5% TRITON X-100, 40 mM sodium citrate, 3 mM MgCl2) and 200 µl beads (50 mg/ml) in a 15 ml centrifuge tube. The mixture was inverted 10 times and incubated at room temperature for 3 minutes, then the tube was placed in a magnet stand (Omega Bio-Tek, Atlanta, Ga.) for 7 minutes. The cell membrane supernatant was carefully removed. 3 ml of nuclear membrane lysis buffer (3.5 M Guanidine Hydrochloride, 20 mM Tris-HCl pH 7.4,) and 10 ul proteinase K (20 mg/ml) was added and incubated at 65° C. for 10 minutes. Then 2 ml of 100% isopropanol was added and the incubation continued for 5 minutes at room temperature. The beads were attracted to the tube wall with the magnet and the supernatant removed. The complex was washed twice with 3 ml 70% EtOH. All of the ethanol was removed and 500 µl water added. To remove residual ethanol the tubes were incubated at 65° C. for 10 minutes with an open lid. The isolated genomic DNA obtained through the present invention is shown in FIG. 3 on EtBr-stained agarose gel electrophoresis.

Figure 4:
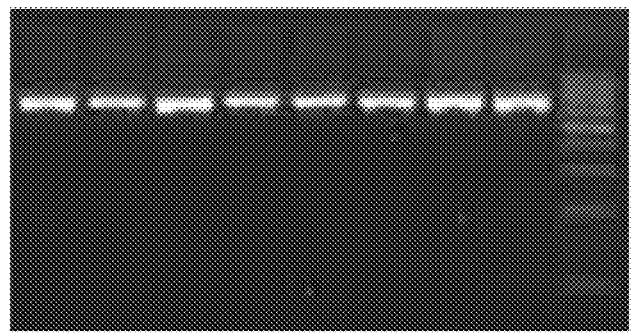
FIG. 4 shows the results on EtBr-stained agarose gel electrophoresis of the separation of PCR amplification products of DNA obtained from 3 ml human whole blood.

PCR amplification: The region for gene coding for human beta-actin was amplified. Amplifications were done using the standard protocols. (See FIG. 4).

Example 3

Isolation of Genomic DNA from Cultured Cells

Cell membrane lysis buffer: 0.01 M phophate buffered isotonic saline (146 mM) with calcium (1.0 mM $CaCl_2$) and magnesium (0.5 mM $MgSO_{4.7}$ $H_2O$) which contained 0.6% NP40 (v/v) (Accurate Scientific and Chemical Co., Hicksville, N.Y.) and 0.2% bovine serum albumin (BSA) (w/v) (Fraction Five GIBCO).

Figure 5:
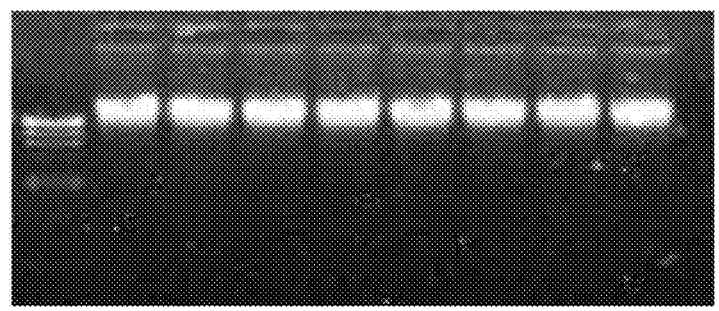
FIG. 5 shows the results on EtBr-stained agarose gel electrophoresis of the separation of genomic DNA obtained from $10^6$ cultured cells.

DNA isolation: $10^6$ Cultured HEK 293 cells (Clontech, Mountain View, Calif. 94043) and Hela cells (ATCC, Manassas, Va. 20108) were mixed with a cell membrane lysis buffer (0.6% NP40 v/v; 0.01 M phosphate buffer saline (146 mM); 1.0 mM CaCl2 and 0.5 mM $MgSO_4$) in a microcentrifuge tube. The mixture was inverted 20 times and incubated at room temperature for 3 minutes, then the tube was placed in a magnet stand (Omega Bio-Tek, Atlanta, Ga.) for 7 minutes. The cell membrane supernatant was carefully removed. 300 µl of nuclear membrane lysis buffer (3.5 M Guanidine Hydrochloride, 20 mM Tris-HCl pH 7.4,) and 10 ul proteinase K was added and incubated at 65° C. for 10 minutes. Then 200 µl of 100% isopropanol was added and the incubation continued for 5 minutes at room temperature. The beads were attracted to the tube wall with the magnet and the supernatant removed. The complex was washed twice with 500 µl 70% EtOH. All of the ethanol was removed and 50 µl water added. To remove residual ethanol the tubes were incubated at 65° C. for 10 minutes with an open lid. The isolated genomic DNA obtained through the present invention is shown in FIG. 5 on EtBr-stained agarose gel electrophoresis.

Example 4

Isolation of Genomic DNA from Mouse Liver

Figure 6:
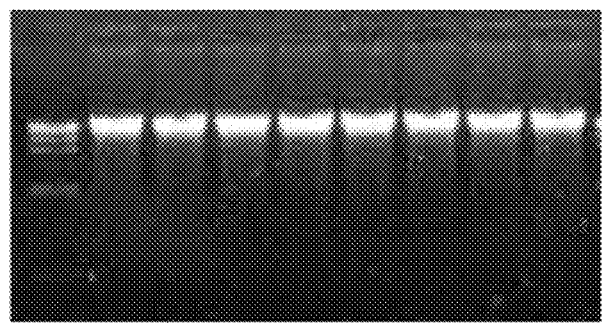
FIG. 6 shows the results on EtBr-stained agarose gel electrophoresis of the separation of genomic DNA obtained from 30 mg fish and frog liver.

DNA Isolation: 30 mg fish and frog liver was mixed with a cell membrane lysis buffer (1% TRITON X-100, 40 mM sodium citrate, 3 mM MgCl2) and 10 µl beads (50 mg/ml) in a microcentrifuge tube. The mixture was inverted 10 times and incubated at room temperature for 3 minutes, then the tube was placed in a magnet stand (Omega Bio-Tek, Atlanta, Ga.) for 7 minutes. The cell membrane supernatant was carefully removed. 300 µl of nuclear membrane lysis buffer (3.5 M Guanidine Hydrochloride, 20 mM Tris-HCl pH 7.4,) and 10 ul proteinase K was added and incubated at 65° C. for 10 minutes. Then 200 µl of 100% isopropanol was added and the incubation continued for 5 minutes at room temperature. The beads were attracted to the tube wall with the magnet and the supernatant removed. The complex was washed twice with 500 µl 70% EtOH. All of the ethanol was removed and 50 µl water added. To remove residual ethanol the tubes were incubated at 65° C. for 10 minutes with an open lid. The isolated genomic DNA obtained through the present invention is shown in FIG. 6 on EtBr-stained agarose gel electrophoresis.

Example 5

Cell Nuclei Bound to Magnetic Beads

U.S. Pat. No. 4,668,618 incorporated by reference herein, demonstrates that under cell membrane lysis conditions similar to certain embodiments described in this invention, only cell membrane are lysed and cell nuclei membrane are kept intact. This study was to confirm that only cell nuclei, not the intact cells, are indeed preferably bound with magnetic beads. Human whole blood from same donor was divided into two set of 3 ml aliquots in 15 ml tube. The first set of blood sample was treated with 7.5 ml cell membrane lysis buffer, as described in the present invention, containing 1% TRITON X-100, 40 mM sodium citrate and 3 mM $MgCl_2$, which only lyses cell membranes and keeps the cell nuclear membrane intact, in the presence of 200 µl beads (50 mg/ml) in a microcentrifuge tube. The second set of blood sample was treated with 15 ml red blood cell lysis buffer containing 8.3 g $NH_4Cl$, 155 mM, 10 mM $KHCO_3$ and 0.1M EDTA, which only lyses the red blood cells and keeps the white blood cells (which contains nucleic acid) intact, in the presence of 200 µl magnetic beads. The mixtures were inverted 10 times and incubated at room temperature for 5 minutes, then the tubes were placed in a magnet stand (Omega Bio-Tek, Atlanta, Ga.) for 7 minutes. The supernatants were carefully removed from the two tubes, respectively.

The blood samples treated with cell membrane lysis buffer was mixed with 3 ml cell nuclear membrane lysis buffer comprising 3.5 M Guanidine Hydrochloride, 20 mM Tris-HCl pH 7.4, and 10 µl proteinase K (20 mg/ml) and incubated at 65° C. for 10 minutes. Then 2 ml of 100% isopropanol was added and the incubation continued for 5 minutes at room temperature. The beads were attracted to the tube wall with the magnet and the supernatants were removed. The complex was washed twice with 3 ml 70% EtOH. All of the ethanol was removed and 500 µl water added. To remove residual ethanol the tubes were incubated at 65° C. for 10 minutes with an open cap.

The blood samples treated with red blood cell lysis buffer were mixed with 3 ml cell lysis buffer comprising 100 mM Sodium Chloride (NaCl), 10 mM EDTA, 50 mM Tris-HCl pH 8.0, 1% SDS, and 50 µl proteinase K (20 mg/ml) and incubated at 65° C. for 10 minutes. Then 2 ml of 100% isopropanol was added and the incubation continued for 5 minutes at room temperature. The beads were attracted to the tube wall with the magnet and the supernatants were removed. The complex was washed twice with 3 ml 70% EtOH. All of the ethanol was removed and 500 µl water added. To remove residual ethanol the tubes were incubated at 65° C. for 10 minutes with an open cap.

The results show that genomic DNA was successfully isolated from the blood samples that were treated with a cell membrane lysis buffer in the first treatment, but no genomic DNA was obtained from the blood samples that were treated with a red blood cell lysis buffer in the second treatment (data no show here). It is known that the human whole blood contains red blood cells which do not have cell nuclei and white blood cells which contain cell nuclei. When the whole blood sample treated with the cell membrane lysis buffer, as described in the present invention, both red blood cell and white blood cell membranes were lysed and cell nuclei from the white blood cells were released and bound to the magnetic beads via magnet stand. Following a cell nuclear membrane lysis treatment, genomic DNA from the lysed white cell nuclei were released and bound to the magnetic beads after the isopropanol precipitation, such genomic DNA was then isolated from the beads through a EtOH and water washing step.

However, when the human whole blood sample was treated with the red blood cell lysis buffer, only red blood cells were lysed, the white blood cells were kept intact. If the magnetic beads would have bound to the intact white blood cells, following the defined cell lysis buffer treatment that can lyse both cell membrane and nuclear membrane, the genomic DNA from the white blood cells would have been obtained. However, no genomic DNA was obtained suggesting that the intact white blood cells do not bind to the magnetic beads, and were removed in the supernatant.

Therefore, these results demonstrated that using the present invention, substantially only cell nuclei, not the whole cells, are bound with magnetic beads after the cell membrane is lysed, and the nucleic acids are isolated from the beads after nucleic membrane is lysed.

Example 6

A comparative study was performed to demonstrate that DNA isolation using the present invention obtains comparable or superior yield and purity as compared to the conventional DNA isolation method which lyse the cell membrane and nuclear membrane at the same time. Using the conventional cell lysis buffer that lyses both cell membranes and nuclear membranes at the same time, one is not able to isolate DNA without further treatment steps to remove RNAase, proteins, etc. that are contaminated with DNA after the initial lysis step. Therefore, the present invention provides a method of separating and/or isolating cell nuclei first from cell membrane supernatant, and then isolating the DNA released from the isolated nuclei without the need for RNase treatment, which significantly reduces the isolation steps and time to remove contaminants during the process, and significantly increase the purity and yield of the DNA that is isolated.

What is claimed is:

1. A method of isolating nucleic acids from a biological sample of cells, comprising:
   a) contacting a sample containing cells with a cell membrane lysis solution in the presence of a solid support coated with negative charge, wherein the cell membrane lysis solution selectively lyses cell membranes over nuclear membranes, and wherein said solid support coated with negative charge binds to intact cell nuclei;
   b) separating intact cell nuclei bound solid support from cell membrane lysis supernatant;
   c) contacting the intact cell nuclei bound to said solid support with a nuclear membrane lysis solution to lyse nuclear membranes, wherein nucleic acids are released from lysed nuclei and bind to said solid support; and
   d) contacting the lysed nuclear membranes and nucleic acid bound solid support with a precipitant to precipitate said nucleic acid bound solid support.

2. The method of claim 1, wherein said solid support comprises spherical particles.

3. The method of claim 2, wherein said spherical particles are monodisperse particles having uniform size and uniform reproducibility of reaction.

4. The method of claim 3, wherein said monodisperse particles are non-magnetic, magnetic, or super paramagnetic polymeric beads.

5. The method of claim 1, wherein said solid support comprises magnetic polymeric beads, and wherein step (b) comprises applying a magnetic field to precipitate cell nuclei-magnetic beads complexes in pellets.

6. The method of claim 5, wherein said magnetic field is a permanent magnet.

7. The method of claim 5, wherein said magnetic polymeric beads are further coated with functionalized surfaces selected from the group consisting of hydrophilic or hydrophobic surfaces, DNA binding proteins, complementary DNA or RNA sequences, zippers, histones, and intercalating dyes.

8. The method of claim 1, wherein said cell membrane lysis solution in step (a) comprises a nonionic surfactant selected from the group consisting of NONIDE P40, TRITON X-100, and octy glycoside, and wherein said nonionic surfactant is within the range of about 0.1 to 5% v/v in said lysis solution.

9. The method of claim 8, wherein said cell membrane lysis solution has a pH of about 5 to 8.

10. The method of claim 8, wherein said cell membrane lysis solution has a pH of about 6.5 to 7.5.

11. The method of claim 8, wherein said cell membrane lysis solution in step (a) comprises 10 mM tris base, pH 7.5-8.0, 0.5% NONIDE P 40, 40 mM sodium citrate, and 3 mM $MgCl_2$.

12. The method of claim 1, wherein said cell nuclear membrane lysis solution in step (c) comprises a detergent, a chaotrope, or a combination thereof.

13. The method of claim 12, wherein said detergent is selected from the group consisting of SDS, LiDS and sarkosyl.

14. The method of claim 12, wherein said chaotrope is selected from the group consisting of guanidium hydrochloride (GHCl), guanidium thiocyanate (GTC), sodium iodide (NaI), perchlorate, and lysis enzymes.

15. The method of claim 12, wherein said cell nuclear membrane lysis solution in step (c) comprises 1% (w/v) sarkosyl and 4M GTC.

16. The method of claim 1, wherein said precipitant in step (d) is selected from the group consisting alcohol, salt, detergent, polyethylene glycol, or a combination thereof.

17. The method of claim 1, further comprising a later step of isolating nucleic acids from said solid support by elution following a washing step.

18. The method of claim 17, wherein said elution comprises heating, leaving said nucleic acids in solution, and removing the solid support from the solution.

19. The method of claim 17, wherein said washing step comprises using a washing media comprising low to moderate ionic strength or alcohols.

20. The method of claim 1, wherein said nucleic acid is DNA.

* * * * *